(12) United States Patent
Sun et al.

(10) Patent No.: US 10,893,946 B2
(45) Date of Patent: Jan. 19, 2021

(54) ASYMMETRIC ARTIFICIAL KNEE JOINT

(71) Applicant: CORENTEC CO., LTD., Cheonan-si (KR)

(72) Inventors: Doo-Hun Sun, Seoul (KR); Jung-Woo Seo, Seoul (KR); Oui-Sik Yoo, Seoul (KR)

(73) Assignee: Corentec Co., Ltd., Cheonan-si (KR)

( * ) Notice: Subject to any disclaimer, the term of this patent is extended or adjusted under 35 U.S.C. 154(b) by 146 days.

(21) Appl. No.: 15/746,291

(22) PCT Filed: Jun. 2, 2016

(86) PCT No.: PCT/KR2016/005842
§ 371 (c)(1),
(2) Date: Jan. 19, 2018

(87) PCT Pub. No.: WO2017/014424
PCT Pub. Date: Jan. 26, 2017

(65) Prior Publication Data
US 2018/0206997 A1 Jul. 26, 2018

(30) Foreign Application Priority Data

Jul. 20, 2015 (KR) .................. 10-2015-0102362

(51) Int. Cl.
*A61F 2/38* (2006.01)
*A61F 2/30* (2006.01)
(52) U.S. Cl.
CPC .......... *A61F 2/3836* (2013.01); *A61F 2/3859* (2013.01); *A61F 2/3886* (2013.01); *A61F 2002/30934* (2013.01)

(58) Field of Classification Search
CPC ...... A61F 2/389; A61F 2/3859; A61F 2/3886; A61F 2/38; A61F 2002/30604; A61F 2002/3895; A61F 2/3868; A61F 2002/3863; A61F 2310/00179; A61F 2310/00011; A61F 2230/0006; A61F 2230/0071; A61F 2002/4205; A61F 2/64; A61F 2002/30736; A61F 2002/2892; A61F 2002/30112;
(Continued)

(56) References Cited

U.S. PATENT DOCUMENTS 4,963,152 A 10/1990 Hofmann et al.
5,413,604 A * 5/1995 Hodge ............... A61F 2/38
623/20.28
5,824,105 A 10/1998 Ries et al.
(Continued)

FOREIGN PATENT DOCUMENTS

JP 2007-222616 A 9/2007
KR 10-0904087 A 6/2009

OTHER PUBLICATIONS

International Search Report dated Sep. 12, 2016, issued in PCT Application No. PCT/KR2016/005842, filed Jun. 2, 2016.
(Continued)

*Primary Examiner* — Ann Schillinger
(74) *Attorney, Agent, or Firm* — Workman Nydegger

(57) ABSTRACT

The present invention relates to an asymmetric artificial knee joint that includes a bearing member having a medial sulcus and a lateral sulcus, and a femoral component having a medial condyle and a lateral condyle and disposed on the bearing member.

14 Claims, 9 Drawing Sheets

(58) Field of Classification Search
CPC .. A61F 2002/30131; A61F 2002/30192; A61F 2002/30332
See application file for complete search history.

(56) References Cited

U.S. PATENT DOCUMENTS

2007/0185581 A1   8/2007  Akizuki et al.
2013/0131817 A1*  5/2013  Parisi .................... A61F 2/3886
                                                          623/20.29
2013/0190884 A1   7/2013  Hashida

OTHER PUBLICATIONS

Written Opinion dated Sep. 12, 2016, issued in PCT Application No. PCT/KR2016/005842, filed Jun. 2, 2016.

* cited by examiner

ASYMMETRIC ARTIFICIAL KNEE JOINT

TECHNICAL FIELD

The present invention relates to an asymmetric artificial knee joint and, more particularly to an asymmetric artificial knee joint including: a bearing member having a medial sulcus and a lateral sulcus; and a femoral component having a medial condyle and a lateral condyle and disposed on the bearing member. The bearing member is formed such that lateral sulcus point of the lateral sulcus is positioned more forward than a medial sulcus point of the medial sulcus, and a distance from a central plane of the bearing member to a medial sulcus-point plane including the medial sulcus point of the medial sulcus is larger than a distance from the central plane of the bearing member to a lateral sulcus point-plane including the lateral sulcus point of the lateral sulcus. The femoral component is formed such that a distance from a central plane of the femoral component to a medial peak-point plane including peak points on the medial condyle is larger than a distance from the central plane of the femoral component to a lateral peak-point plane including peak points on the lateral condyle, in order to prevent inwardly biased wear of the bearing by moving the artificial knee joint on the medial sulcus of the bearing member and the medial condyle of the femoral component and to uniformly distribute load applied to the knee to the medial and lateral sides of the knee.

BACKGROUND ART

A knee joint, which is a joint composed of three bones of the femur, the tibia, and the patella surrounding a knee, is a very important joint supporting the weight of a human body and is related to motions using the legs, such as walking or running through joint motion. There is the articular cartilage at the end of the femur and there is the meniscus at the end of the tibia, but when the cartilage is damaged due to strenuous exercise or aging, the bones come in direct contact with each other and a severe pain may be caused.

Total knee arthroplasty is an operation wherein the knee joint is removed by cutting off portions of the femur and the tibia and then an artificial knee joint is implanted by connecting a femoral component 91 to an end of the femur F, inserting and fixing a tibia member 93 in the end of the tibia T, and then installing a bearing member 95 on the tibia member 93 FIG. 1 shows flexion of a knee after total knee arthroplasty and a technology related to FIG. 1 has been disclosed in Korean Patent No. 10-1184905 (2012 Sep. 20).

A virtual central cut surface for dividing a human body to the left and right parts is called a sagittal plane, and with respect to any one of left and right legs, the inner side of the knee positioned at the sagittal plane is called a medial side and the outer side of the knee positioned on the opposite side of the sagittal plane is called a lateral side.

In general, a femoral component includes a lateral condyle positioned at the outer side and having an articular surface, a medial condyle positioned at the inner side and having an articular surface, and a cam connecting the lateral condyle and the medial condyle. The top at the center of the curved articular surface is called a peak.

A bearing member usually includes a lateral sulcus positioned at the outer side and having an articular surface, a medial sulcus positioned at the inner side and having an articular surface, and a post positioned between the lateral sulcus and the medial sulcus.

In the related art, the femoral component of artificial knee joints has a lateral condyle and a medial condyle symmetrically arranged with a cam therebetween and the bearing member is also symmetrically formed with a post therebetween, so abduction (external rotation) that is accompanied by rotation and roll-back around the lateral condyle of the femoral component occurs in flexion of a knee. According to clinically examined results, when a knee performs a motion, a larger load is applied to the medial side at a ratio of 1:2~3 between the lateral side and the medial side. Accordingly, after an artificial knee joint is implanted, the medial sulcus is worn or damaged earlier than the lateral side of the bearing member, so it has been required to develop a technology for solving this problem. FIG. 2 shows a knee joint in abduction, which has been disclosed in Korean Patent Application Publication No. 10-2013-0102034 (2013 Sep. 16).

Further, referring to FIG. 3, in abduction of a femoral component, it has frequently occurred that a cam 911 of a femoral component 91 hits against the edge of a post 951 of a bearing member 95, thereby damaging the bearing member 95. The reason for the damage is because the post 951 of the bearing member 95 has a left-right symmetric structure.

Accordingly, it is required to develop a technology that prevents inward wear of a joint by preventing concentration of load on the medial side of a knee and prevents shock to a post edge of a bearing member by increasing the contact area between the cam of a femoral component and the post of a bearing member.

DISCLOSURE

Technical Problem

The present invention has been made in an effort to solve the problems.

An object of the present invention is to provide an artificial knee joint that can prevent damage and wear of a medial sulcus of a bearing member and accomplish anatomical knee motion of a human body by making a medial condyle of a femoral component and the medial sulcus of the bearing member as the center of motion.

Another object of the present invention is to provide an artificial knee joint in which a lateral condyle can move forwardly more than a medial condyle such that a femoral component can be adducted in flexion of a knee, thereby increasing stability of joint motion by tensioning tissues around a knee joint.

Another object of the present invention is to provide an artificial knee joint in which a lateral sulcus point that is a peak point of a lateral sulcus is positioned more forward than a medial sulcus point that is a peak point of a medial sulcus such that a lateral condyle can move forwardly more than a medial condyle and a femoral component can be adducted, thereby increasing stability of joint motion by tensioning tissues around the knee joint.

Another object of the present invention is to provide an artificial knee joint in which a posterior condyle of a lateral condyle has various curvatures in comparison to a posterior condyle of a medial condyle in a femoral component such that the lateral condyle can move forwardly more than the medial condyle and the femoral component can be adducted, thereby increasing stability of joint motion by tensioning tissues around the knee joint.

Another object of the present invention is to provide an artificial knee joint in which curvatures of a posterior condyle of a lateral condyle increase toward a posterior direction in a femoral component such that the lateral condyle can move forwardly more than the medial condyle and the femoral component can be adducted, thereby increasing stability of joint motion by tensioning tissues around the knee joint.

Another object of the present invention is to provide an artificial knee joint in which a bearing member is asymmetrically formed such that a posterior surface of the bearing member is inclined from a lateral surface to a medial surface in order that that a femoral component that is adducting can be abducted to follow the anatomical structure of human body.

Another object of the present invention is to provide an artificial knee joint in which a posterior protrusion of a lateral sulcus has a curvature smaller than a curvature of a posterior protrusion of a medial sulcus in a bearing member such that a femoral component that is adducting can be abducted to follow the anatomical structure of human body.

Another object of the present invention is to provide an artificial knee joint in which a femoral component is formed such that a distance from a central plane of the femoral component to a medial peak-point plane including peak points on a medial condyle is larger than a distance from the central plane of the femoral component to a lateral peak-point plane including peak points on a lateral condyle, whereby it is possible to prevent damage and wear of a medial sulcus of a bearing member by reducing load that is concentrated on the medial sulcus.

Another object of the present invention is to provide an artificial knee joint in which a bearing member is formed such that a distance from a central plane of the bearing member to a medial sulcus-point plane including a medial sulcus point of a medial sulcus is larger than a distance from the central plane of the bearing member to a lateral sulcus point-plane including a lateral sulcus point of a lateral sulcus, whereby it is possible to prevent damage and wear of a medial sulcus of the bearing member by reducing load that is concentrated on the medial sulcus.

Another object of the present invention is to provide an artificial knee joint in which when a central plane of a bearing member and a central plane of a femoral component are aligned, the distance from the central planes to a medial peak-point plane is the same as the distance from the central planes to a medial sulcus-point plane, and the distance from the central planes to a lateral peak-point plane is the same as the distance from the central plane to a lateral sulcus-point plane such that the femoral component is placed in position on the bearing member.

Another object of the present invention is to provide an artificial knee joint in which a bearing member is asymmetrically formed such that a posterior surface is inclined from a lateral surface to a medial surface in order that a cam surface of a femoral component comes in contact with the asymmetric posterior surface of the post of the bearing member in a wide area when a femoral component that is adducting changes into abduction following the anatomical structure of human body, whereby it is possible to prevent large shock from being applied to a post edge of the bearing member from the cam of the femoral component.

Technical Solution

The present invention has the following configuration to achieve the objects.

An artificial knee joint according to an aspect of the present invention includes a bearing member having a medial sulcus and a lateral sulcus, in which a lateral sulcus point of the lateral sulcus is positioned more forward than a medial sulcus point of the medial sulcus such that the medial sulcus is a center of motion, thereby preventing inwardly biased wear of the bearing member.

The lateral sulcus point may be positioned at a 10~25% anterior point of an AP length connecting an anterior point to a posterior point of the bearing member.

The bearing member may be formed such that a distance from a central plane of the bearing member to a medial sulcus-point plane including the medial sulcus point of the medial sulcus is larger than a distance from the central plane of the bearing member to a lateral sulcus point-plane including the lateral sulcus point of the lateral sulcus.

In the bearing member, a posterior protrusion of the lateral sulcus may have a curvature smaller than a curvature of a posterior protrusion of the medial sulcus.

The bearing member may be asymmetrically formed such that a posterior surface of the bearing member is inclined from a lateral surface to a medial surface.

An artificial knee joint according to another aspect of the present invention includes a femoral component having a medial condyle and a lateral condyle, in which the lateral condyle moves forwardly longer than the medial condyle and the femoral component is adducted, in the femoral component, in flexion of a knee.

The femoral component may be formed such that a distance from a central plane of the femoral component to a medial peak-point plane including peak points on the medial condyle is larger than a distance from the central plane of the femoral component to a lateral peak-point plane including peak points on the lateral condyle.

In the femoral component, a lateral posterior condyle of the lateral condyle may have various curvatures in comparison to a medial posterior condyle of the medial condyle.

In the femoral component, the curvatures of the lateral posterior condyle of the lateral condyle may increase toward a posterior direction.

An artificial knee joint according to another aspect of the present invention includes: a bearing member having a medial sulcus and a lateral sulcus; and a femoral component having a medial condyle and a lateral condyle and placed on the bearing member, in which a lateral sulcus point of the lateral sulcus is positioned more forward than a medial sulcus point of the medial sulcus in the bearing member, the lateral condyle moves forwardly more than the medial condyle and the femoral component is adducted, and the medial sulcus of the bearing member and the medial condyle of the femoral component form a center of motion.

The bearing member may be formed such that a distance from a central plane of the bearing member to a medial sulcus-point plane including the medial sulcus point of the medial sulcus is larger than a distance from the central plane of the bearing member to a lateral sulcus point-plane including the lateral sulcus point of the lateral sulcus, and the femoral component may be formed such that a distance from a central plane of the femoral component to a medial peak-point plane including peak points on the medial condyle is larger than a distance from the central plane of the femoral component to a lateral peak-point plane including peak points on the lateral condyle.

When the central plane of the bearing member and the central plane of the femoral component are aligned, the distance from the central plane of the bearing member to the medial sulcus-point plane including the medial sulcus point of the medial sulcus may be the same as the distance from the central plane of the femoral component to the medial peak-point plane including the peak points on the medial condyle, and the distance from the central plane of the bearing member to the lateral sulcus point-plane including the lateral sulcus point of the lateral sulcus may be the same as the distance from the central plane of the femoral component to the lateral peak-point plane including the peak points on the lateral condyle.

The femoral component may include a cam connecting the medial condyle and the lateral condyle to each other, the bearing member may be asymmetrically formed such that a posterior surface of the bearing member is inclined from a lateral surface to a medial surface, and an inclination of the posterior surface of the post may be the same as an angle that is formed by abduction of the femoral component at the moment when the cam of the femoral component comes in contact with the post.

Advantageous Effects

According to the present invention, it is possible to achieve the following effects from the configuration, combination, and operation relationship described below.

According to the present invention, it is possible to prevent damage and wear of a medial sulcus of a bearing member and to enable anatomical knee motion of a human body by making a medial condyle of a femoral component and the medial sulcus of the bearing member as the center of motion.

Further, since the lateral condyle moves forwardly more than the medial condyle such that a femoral component can be adducted in flexion of a knee, it is possible to increase stability of joint motion by tensioning tissues around a knee joint.

Further, since the lateral sulcus point that is a peak point of a lateral sulcus is positioned more forward than the medial sulcus point that is a peak point of a medial sulcus such that the lateral condyle can move forwardly more than the medial condyle and the femoral component can be adducted, it is possible to increase stability of joint motion by tensioning tissues around the knee joint.

Further, since the posterior condyle of the lateral condyle has various curvatures in comparison to the posterior condyle of the medial condyle in a femoral component such that the lateral condyle can move forwardly more than the medial condyle and the femoral component can be adducted, it is possible to increase stability of joint motion by tensioning tissues around the knee joint.

Further, since the curvatures of the posterior condyle of the lateral condyle increase toward a posterior direction in a femoral component such that the lateral condyle can move forwardly more than the medial condyle and the femoral component can be adducted, it is possible to increase stability of joint motion by tensioning tissues around the knee joint.

Further, since the bearing member is asymmetrically formed such that the posterior surface of the bearing member is inclined from the lateral surface to the medial surface, a femoral component that is adducting can be abducted to follow the anatomical structure of human body.

Further, since the posterior protrusion of a lateral sulcus has a curvature smaller than a curvature of the posterior protrusion of the medial sulcus in the bearing member, a femoral component that is adducting can be abducted to follow the anatomical structure of human body.

Further, since the femoral component is formed such that the distance from the central plane of the femoral component to the medial peak-point plane including peak points on the medial condyle is larger than the distance from the central plane of the femoral component to the lateral peak-point plane including peak points on the lateral condyle, it is possible to prevent damage and wear of a medial sulcus of a bearing member by reducing load that is concentrated on the medial sulcus.

Further, since the bearing member is formed such that the distance from the central plane of the bearing member to the medial sulcus-point plane including the medial sulcus point of the medial sulcus is larger than the distance from the central plane of the bearing member to the lateral sulcus point-plane including the lateral sulcus point of the lateral sulcus, it is possible to prevent damage and wear of a medial sulcus of a bearing member by reducing load that is concentrated on the medial sulcus.

Further, since when the central plane of a bearing member and the central plane of a femoral component are aligned, the distance from the central planes to the medial peak-point plane is the same as the distance from the central planes to the medial sulcus-point plane, and the distance from the central planes to the lateral peak-point plane is the same as the distance from the central plane to the lateral sulcus-point plane, the femoral component can be placed in position on the bearing member.

Further, since the bearing member is asymmetrically formed such that the posterior surface is inclined from the lateral surface to the medial surface in order that the cam surface of the femoral component comes in contact with the asymmetric posterior surface of the post of the bearing member in a wide area when the femoral component that is adducting changes into abduction following the anatomical structure of human body, it is possible to prevent large shock from being applied to a post edge of the bearing member from the cam of the femoral component.

BEST MODE

Hereinafter, preferred embodiments of an asymmetric artificial knee joint according to the present invention will be described in detail with reference to the accompanying drawings. In describing the present invention, well-known functions or constructions will not be described in detail since they may unnecessarily obscure the understanding of the present invention. Unless specifically defined, all terms used herein are the same as the general meanings of corresponding terms that those skilled in the art understand, and if they conflict with the meanings of terms used herein, they follow the definition used herein.

It should be noticed that the drawings for illustrating the present invention show an artificial knee joint that is inserted into the left knee from the sagittal plane.

Figure 4:
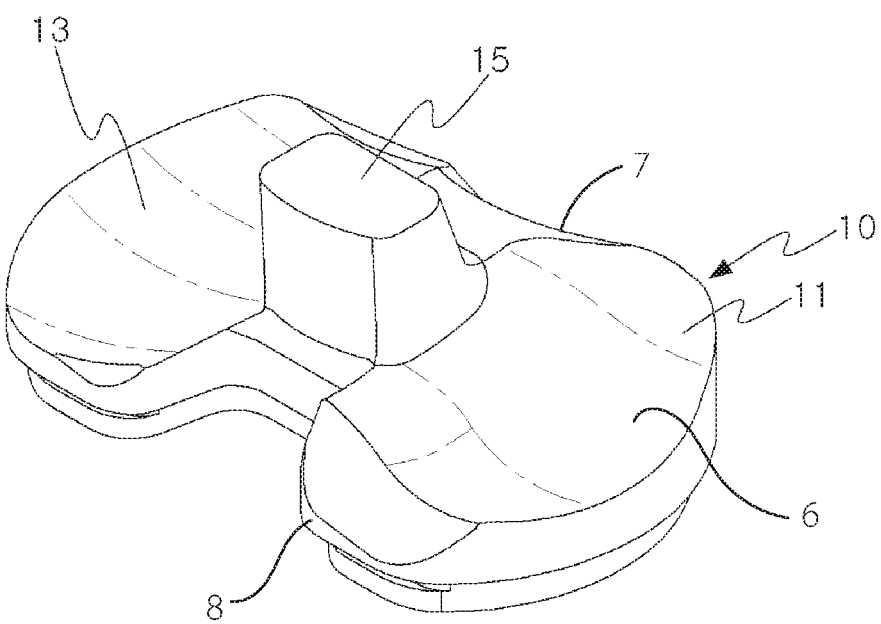
FIG. 4 is a perspective view of a bearing member of the present invention.

FIG. 4 is a perspective view of a bearing member of the present invention. Referring to FIG. 4, a bearing member 10 of the present invention is a component that is disposed on a tibial component connected to femur-sided end of the tibia in total knee arthroplasty to support a femoral component 30. Preferably, the bearing member 10 is a part having an articular surface that allows for translation, rotation, and roll-back of the femoral component 30 on the bearing member 10, depending on motions of the femur in knee motion. The material of the bearing member 10 is not specifically limited, but may be preferably polyethylene.

The bearing member 10 has a top surface 6 that extends between an anterior edge 7 and an opposing posterior edge 8. Recessed into top surface 6 is a medial sulcus 11 and a lateral sulcus 13. A post 15 centrally upstands from top surface 6.

The medial sulcus 11, which is intended to support the medial condyle 31 of the femoral component 30 in contact therewith, forms an articular surface. Preferably, the medial sulcus 11 is a recess for receiving the medial condyle of the femoral component 30 having a convex surface, in which the maximally recessed portion is referred to as a sulcus point and the sulcus point on the medial sulcus 11 is referred to as a medial sulcus point 111 to be discriminated from a lateral sulcus 13 to be described below (see FIG. 7).

Figure 5:
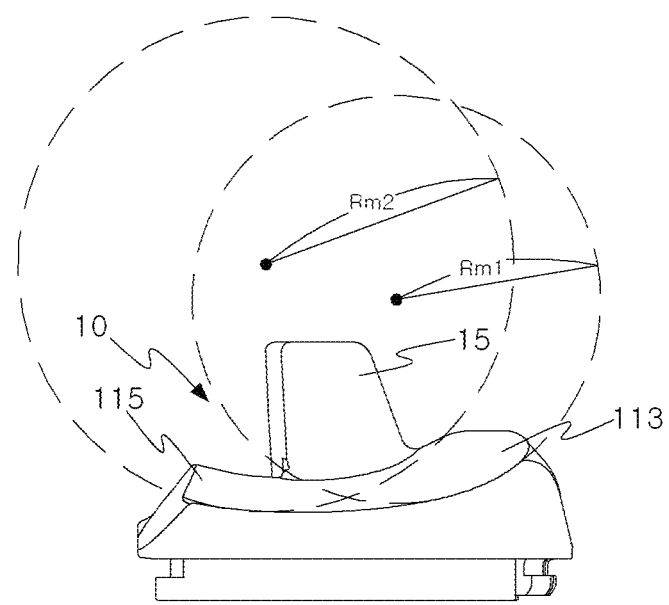
FIG. 5 is a side view showing the curvature of a medial sulcus.

FIG. 5 is a side view showing the medial sulcus. Referring to FIG. 5, the side of the medial sulcus 11 is generally formed in a concave shape and the medial sulcus 11 can be divided into a medial anterior section 113 and a medial posterior section 115 due to different side curvatures.

The medial anterior section 113 is a part having a predetermined curvature and protruding forward from the medial sulcus 11 and the medial posterior section 115 is a part having a predetermined curvature and protruding rearward from the medial sulcus 11. The large curvatures ahead of and behind the medial sulcus point 111 of the medial sulcus 11 prevent a medial condyle 31 of the femoral component 30 (described below) that is placed on the medial sulcus 11 from being disjointed forward and rearward, help the medial condyle 31 of the femoral component 30 that is placed on the bearing member 10 be placed in position, and limit the distance of translation of the medial condyle 31 of the femoral component 30, so it is possible to accomplish the objective knee motion of the present invention around the medial sulcus 11 and the medial condyle 31.

The anterior curvature of the medial anterior section 113 allows for rotation of the femoral component 30 through the medial anterior section 113 in the flexion of the knee, and as shown in the figure, it is preferable that the curvature at the anterior portion of the medial sulcus 11 is larger than the curvature at the posterior portion (the radius of curvature Rm1 at the anterior portion is smaller than the radius of curvature Rm2 at the posterior portion).

The lateral sulcus 13, which is intended to support the lateral condyle 33 of the femoral component 30 in contact therewith, forms an articular surface, similar to the medial sulcus 11. Preferably, the lateral sulcus 13 is a recess for receiving the lateral condyle 33 of the femoral component 30, in which the maximally recessed sulcus point of the lateral sulcus 13 is referred to as the lateral sulcus point 131 (see FIG. 7).

Figure 6:
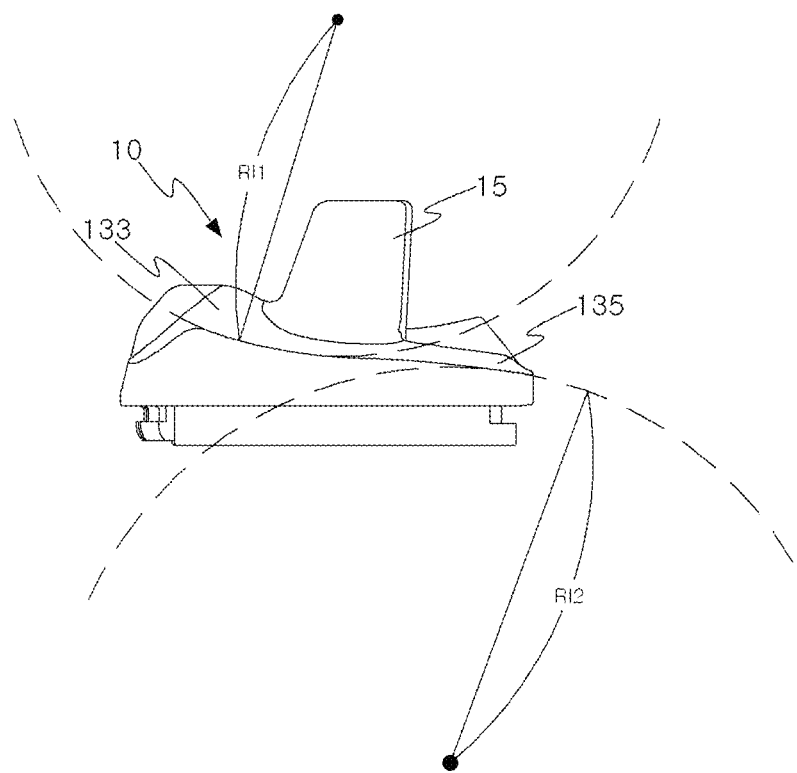
FIG. 6 is a side view showing the curvature of a lateral sulcus.

FIG. 6 is a side view showing the curvature of the lateral sulcus. Referring to FIG. 6, in the lateral sulcus 13 of the bearing member 10, the anterior portion may have a positive (+) side curvature and the posterior portion may have a negative (−) side curvature. Due to the different side curvatures, the lateral sulcus 13 is divided into a lateral anterior section 113 and a later posterior section 135.

The later anterior section 133 is a part having a predetermined positive (+) side curvature (a radius of curvature R11) and protruding forward from the lateral sulcus 13 and the lateral posterior section 135 is a part inclined with a negative (−) side curvature (a radius of curvature R12) at the posterior portion of the lateral sulcus 13. By this shape, the lateral condyle 33 of the femoral component 30 (described below) that is placed on the lateral sulcus 13 can perform translation and rotation over a longer distance than the medial condyle 31, so it is possible to achieve the objective knee motion of the present invention around the medial sulcus 11 and the medial condyle 31.

Longer distance translation of the lateral condyle 33 may be considered as conflicting with the anatomical structure of human body in which abduction (external rotation) occurs in flexion of a knee, but adduction (internal rotation) occurs around the medial sulcus 11 and the medial condyle 31, the tissues around the joint are tightened, stability of the artificial knee joint can be increased. Further, since the curvature (radius of curvature R12) of the lateral posterior section 135 is smaller than the curvature (radius of curvature Rm2) of the medial posterior section 115 (radii of curvature R12>Rm2), adduction of the femoral component 30 that is converted into abduction following the anatomical structure of human body.

Figure 7:
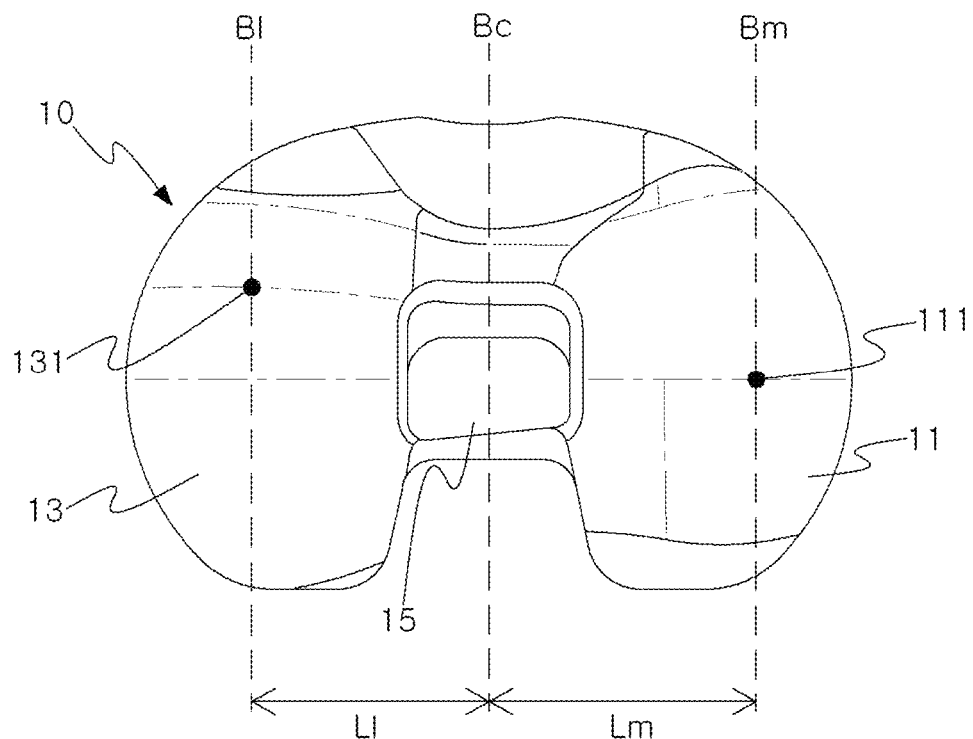
FIG. 7 is a view showing the positions of a lateral sulcus point and a medial sulcus point of the bearing member.

FIG. 7 is a view showing the positions of the lateral sulcus point and the medial sulcus point on the bearing member. Referring to FIG. 7, the lateral sulcus point 131 is positioned more forward than the medial sulcus point 111 on the bearing member. This is for preventing medially biased wear of the bearing member 10 by making the medial sulcus 11 be the center of motion.

In detail, it may be preferable that the lateral sulcus point 131 is positioned at a 10~25% anterior point of an AP length connecting the anterior point to the posterior point of the bearing member 10.

Referring to FIG. 7, assuming that a virtual vertical plane including the medial sulcus point 111 defined as a medial sulcus-point plane Bm, a virtual vertical plane including the lateral sulcus point 131 defined as a lateral sulcus-point plane B1, and a virtual vertical plane including the center between the medial surface and the lateral surface of the post 15 (described below) of the bearing member 10 is defined as a central plane Bc, the distance Lm from the central plane Bc to the medial sulcus-point plane Bm is larger than the distance L1 from the central plane Bc to the lateral sulcus-point plane B1 in the bearing member 10.

Moment of force means the product of the distance of force from a predetermined position and the magnitude of the force, and when force F is applied to a plane, force acting on a point A spaced to the left by m from the point where the force F is applied and force acting on a point P spaced to the right by n from the point where the force F is applied are respectively np/(m+n) and mp/(m+n), in which when m is smaller than n, relatively small force acts on the point B.

That is, smaller force is applied to points spaced farther from the point where reference force acts. Accordingly, the problem in the related art that two- or three-time larger force is applied to a medial portion than a lateral portion can be removed by making the distance Lm from the central plane Bc to the medial sulcus-point plane Bm larger than the distance L1 from the central plane Bc to the lateral sulcus-point plane B1.

Accordingly, the present invention intends to uniformly distribute load by positioning the lateral sulcus point 131 more forward than the medial sulcus-point 111 such that the medial sulcus is the center of knee motion in the bearing member 10 and positioning the medial sulcus point 111 farther than the lateral sulcus point 131 from the central plane Bc of the bearing member.

Figure 8:
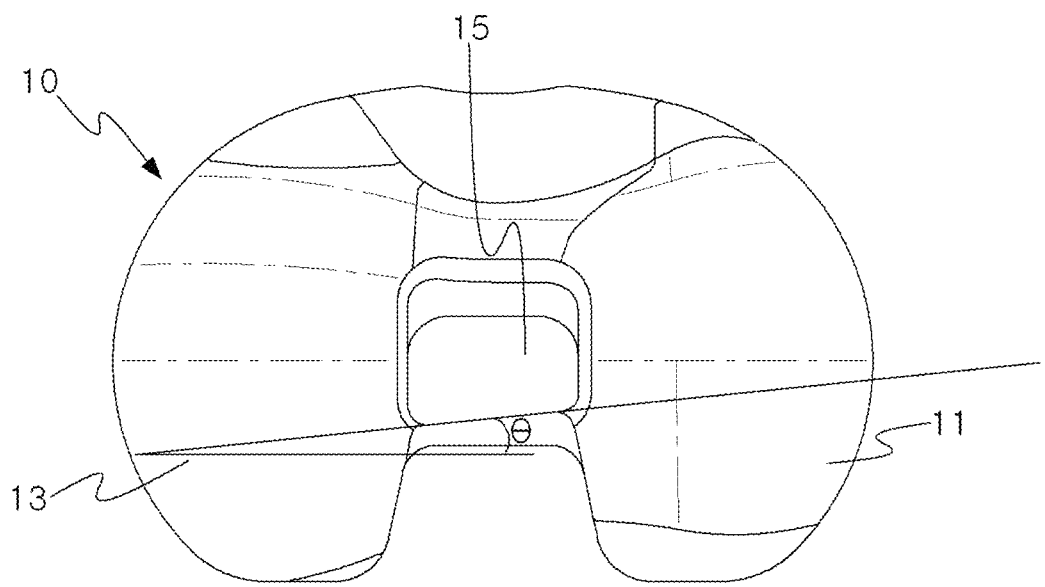
FIG. 8 is a view showing an inclination of a rear side of a post.

The post 15 protrudes between the medial sulcus 11 and the lateral sulcus 13 on the bearing member 10. For the convenience of description, the post 33 is divided into one top and four sides and the four sides can be defined as a medial surface facing the medial sulcus 11, a lateral surface facing the lateral sulcus 13, an anterior surface facing the anterior portion (where the patella is positioned) of the bearing member 10, and a posterior surface facing the posterior portion (opposite to the position of the patella) of the bearing member 10. The post 15 of the present invention is described on the basis of this division. The post 15 has an asymmetric shape in which the posterior surface is inclined from the lateral surface to the medial surface. FIG. 8 shows the inclination of the posterior surface of the post. Referring to FIG. 8, it can be seen that the lower side of the top makes a predetermined angle θ from the lateral surface to the medial surface.

Figure 1:
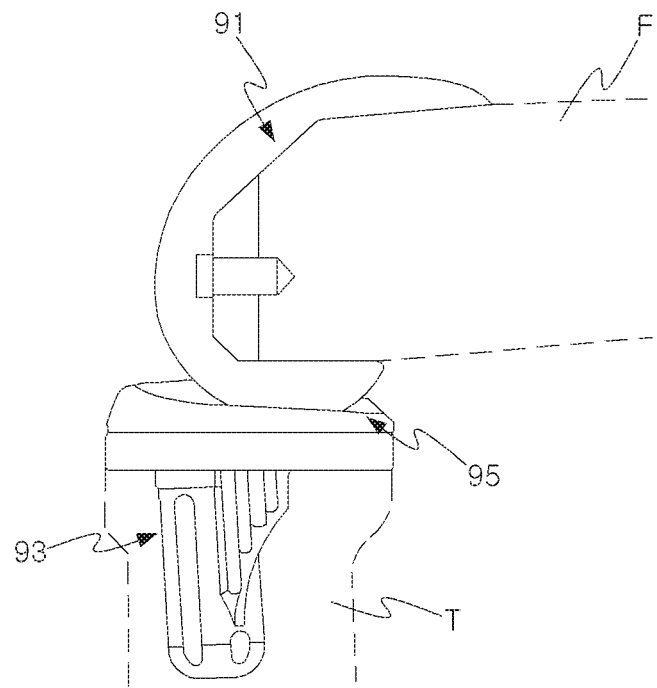
FIG. 1 is a view showing flexion of a knee after artificial knee joint implantation.
Figure 2:
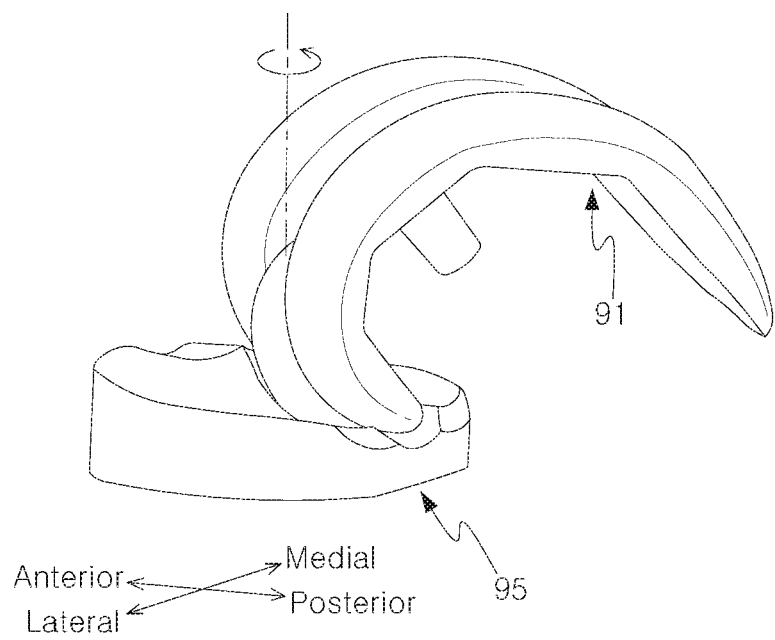
FIG. 2 is a view showing a knee joint in abduction.
Figure 3:
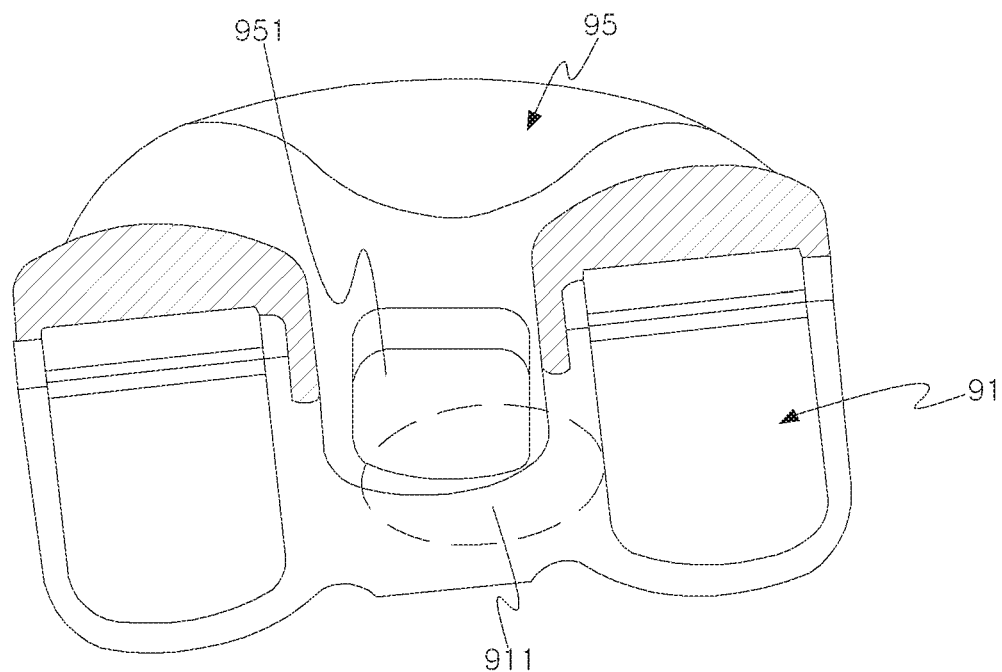
FIG. 3 is a view showing that a cam of a femoral component hits against a post edge of a bearing member.

According to the artificial knee joint of the related art described above, when the femoral component 30 to be described below is adducted, as shown in FIG. 3, a cam meets the posterior surface of the post 15 in a narrow contact area, so stress concentration occurs and the edge of the post is strongly shocked. Accordingly, there is a need for preventing the stress concentration by increasing the contact area, and to this end, it is preferable that the bottom side of the top of the post 15 is inclined at an angle θ, that is, the post is asymmetrically formed such that the posterior surface is inclined from the lateral surface to the medial surface.

The inclination θ of the posterior surface of the post is made the same as the inclination generated by abduction of the femoral component 30 at the moment when a cam 35 (described below) of the femoral component 30 comes in contact with the post 15 to increase the contact area between the post 15 and the cam 35.

Figure 9:
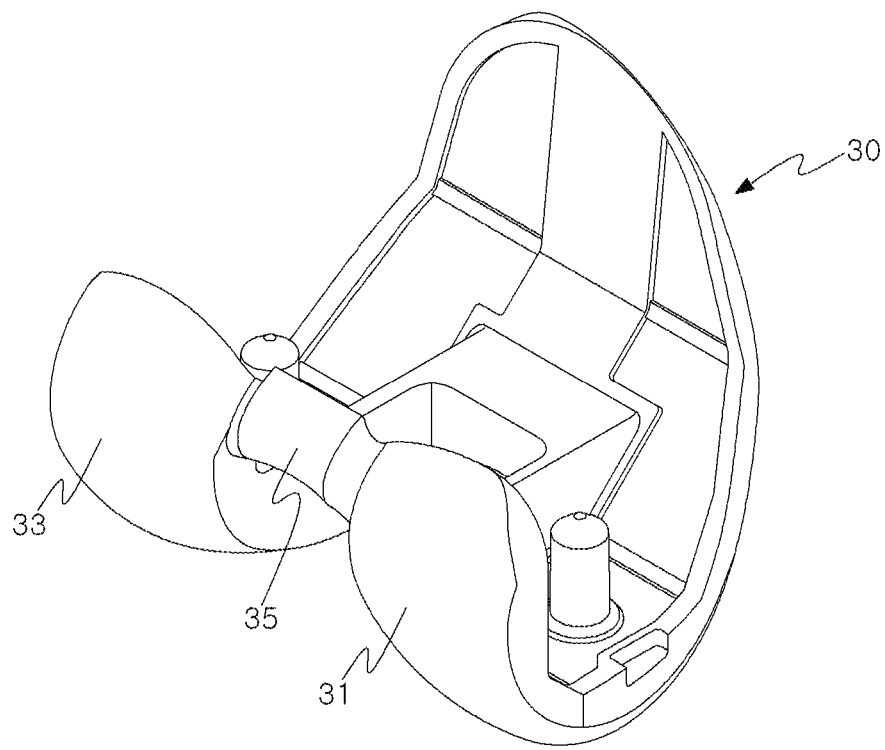
FIG. 9 is a perspective view of a femoral component of the present invention.

FIG. 9 is a perspective view of a femur component of the present invention. Referring to FIG. 9, the femoral component 30 of the present invention, which is intended to be coupled to the tibia-sided end of a femur in total knee arthroplasty, is placed on the top of the bearing member 10 to be supported by the bearing member 10 and makes translation, rotation, and roll-back in knee motion, and the lateral surface of the femoral component 30 forms an articular surface to allow for these motions. In detail, the femoral component can be considered as having a shape similar to the spherical projection at the end of the femur in the human body. The material of the femoral component is not specifically limited, but preferably, titanium may be used.

The femoral component 30 includes a medial condyle 31, a lateral condyle 33, and a cam 35.

Figure 10:
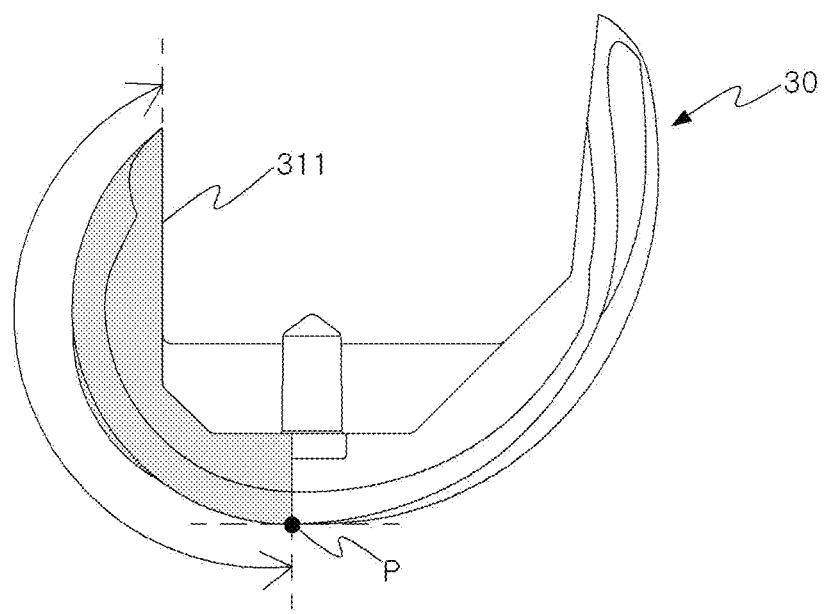
FIG. 10 is a view showing a posterior condyle and a peak contact point of the femoral component.

The medial condyle 31 means the part that is brought in contact with the medial sulcus 11 of the bearing member 10, close to the sagittal plane, in the femoral component 30, and preferably, it has a smooth convex articular surface to be stably seated in the medial sulcus 11 that is a recess. FIG. 10 is a view showing a posterior condyle and a peak contact point of the femoral component. When the femoral component 30 of the present invention is placed in position on the bearing member 10, the peak point being in contact with the bearing member 10 of peak points on the medial sulcus 11 is referred to as the peak contact point P, and the section from the peak contact point P to the end bending up to the posterior portion of the femoral component 30 is referred to as the posterior condyle. The posterior condyles are divided into a medial posterior condyle 311 that is the posterior condyle of the medial condyle 31 and a lateral posterior condyle 331 that is the posterior condyle of the lateral condyle 33. The dark portion is the medial posterior condyle 311 in FIG. 10.

Figure 11:
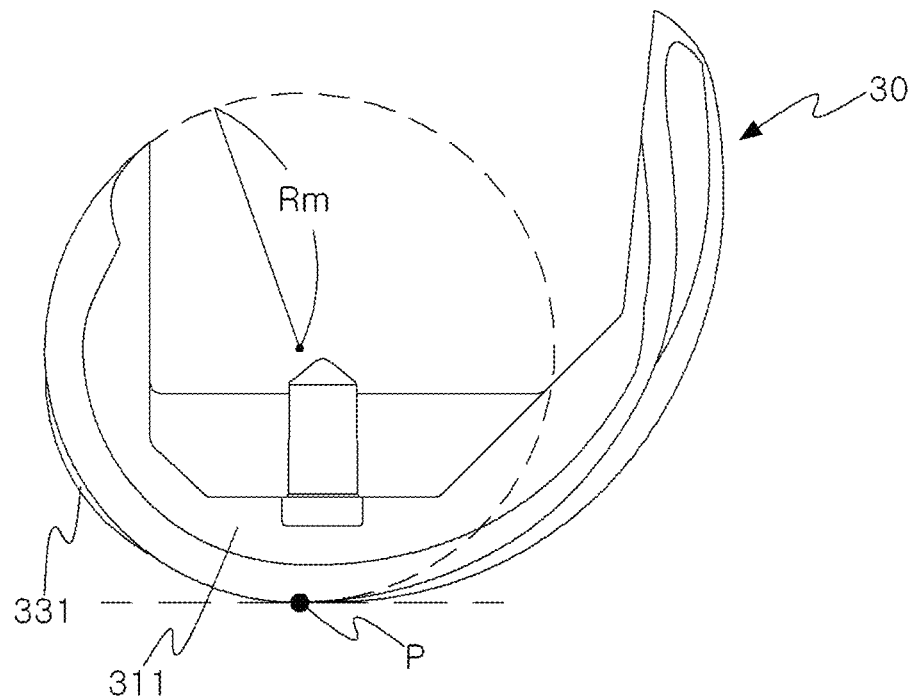
FIG. 11 is a side view showing the curvature of a medial posterior condyle.

FIG. 11 is a side view showing the curvature of the medial posterior condyle. Referring to FIG. 11, the medial posterior condyle 311 may have one curvature (radius of curvature Rm). The present invention is technologically characterized in that the lateral condyle 33 can move forwardly more than the medial condyle 31 such that the femoral component 30 can be adducted on the bearing member 10, thereby tensioning the tissues around a knee joint and increasing stability in knee motion. Accordingly, as shown in the figure, the medial posterior condyle 311 is given one curvature to be the center of knee motion by making uniform rotation and roll-back.

Figure 12:
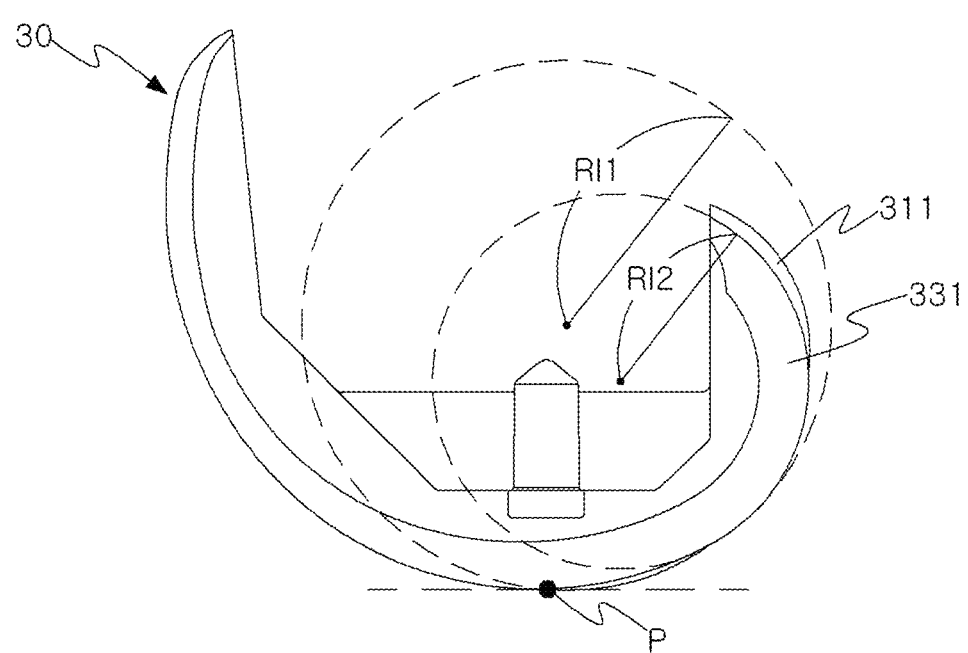
FIG. 12 is a side view showing the curvature of a lateral posterior condyle.

The lateral condyle 33 means the part that is brought in contact with the lateral sulcus 13 of the bearing member 10, farther from the sagittal plane, in the femoral component 30, and preferably, it has a smooth convex articular surface to be stably seated in the lateral sulcus 13 that is a recess. FIG. 12 is a side view showing the curvatures of the lateral posterior condyle. Referring to FIG. 12, it can be seen that as compared with the medial posterior condyle 311 having one curvature, the lateral posterior condyle 331 has a plurality of curvatures.

Referring to FIG. 12, the radius of curvature at the peak contact point P is R11, but the radius of curvature at the posterior end of the lateral condyle 33 is R12. R11 is larger than R12 such that the curvature of the lateral posterior condyle 331 increases toward a posterior direction of the femoral component 30.

Accordingly, adduction (internal rotation) in which the lateral condyle 33 moves forwardly more is generated at the early stage of flexion of a knee, and the motion is changed into abduction (external rotation) after the point where the curvature is changed. This is for preventing the present invention designed to adduct the femoral component 30 to prevent medial wear of a knee from causing various side effects after an operation by conflicting with the anatomical structure of human body that makes abduction.

Figure 13:
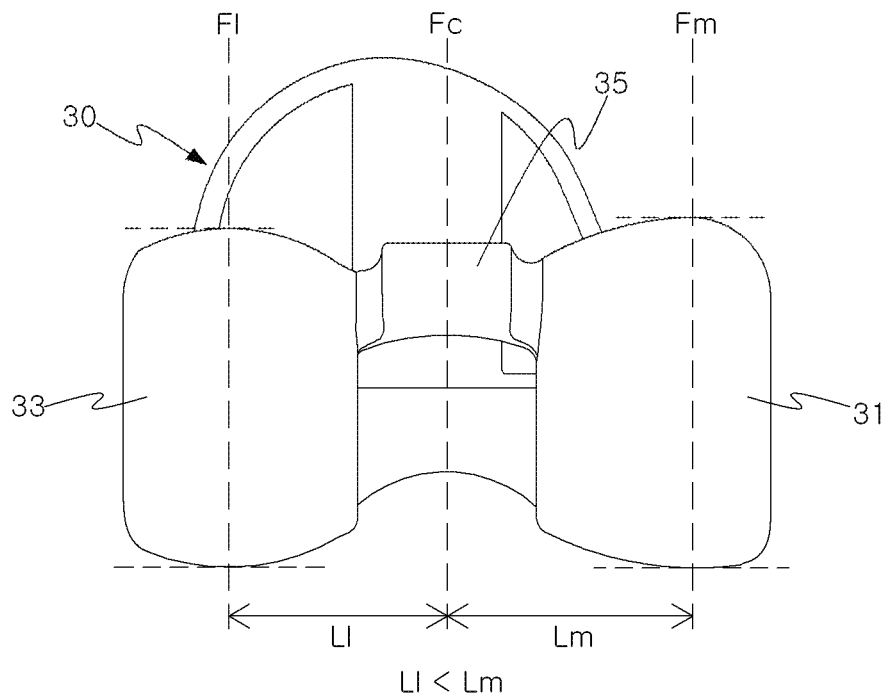
FIG. 13 is a view showing the positions of a medial peak point and a lateral peak point of the femoral component.

FIG. 13 is a view showing the positions of a medial peak point and a lateral peak point of the femur coupler. Referring to FIG. 13, the distance Lm from a virtual central plane Fc including the center of the cam 35 of the femoral component 30 to a medial peak-point plane Fm that is a virtual vertical plane including the peak points on the articular surface of the medial condyle 31 is longer than the distance L1 from the virtual central plane Fc to the lateral peak-point plane F1 that is a virtual vertical plane including the peak points on the lateral condyle 33. This is because when force F is applied, force acting on a point A spaced left by m from the point where the force F is applied and force acting on a point P spaced right by n from the point where the force F is applied are respectively np/(m+n) and mp/(m+n), in which when m is smaller than n, relatively small force acts on the point B. Accordingly, the distance Lm from the virtual central plane Fc including the center of the cam 35 to the medial peak-point plane Fm is made longer than the distance L1 to the lateral peak-point plane F1 to prevent inwardly biased force and uniformly distribute load to the medial and lateral sides of a knee.

The cam 35 is disposed between the medial condyle 31 and the lateral condyle 33 to connect them and prevent dislocation of the femoral component 30 rotating on the bearing member 10.

The cam 35 may connect the posterior ends of the medial and lateral condyles 31 and 33 in the femoral component 10 to minimize a limit in bending angle of a knee due to interference with the post 15 protruding on the bearing member 10 in flexion of the knee (see FIG. 9).

Figure 14:
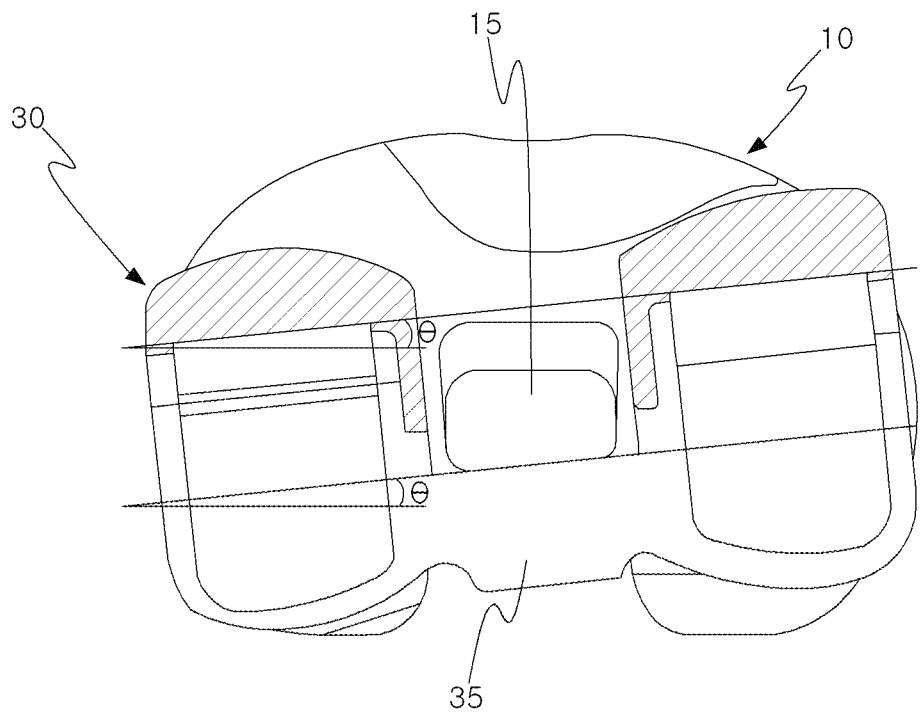
FIG. 14 is a view showing the moment when a cam and a post meet each other.

FIG. 14 is a view showing the moment when the cam and the post meet each other. Referring to FIG. 14, according to the artificial knee joint described above in the related art, the post and the cam 35 come in contact with each other in a narrow contact area, so large stress concentration is caused and the edge of the post is strongly shocked. Accordingly, there is a need for preventing stress concentration by increasing the contact area, and to this end, the post 15 is asymmetrically formed such that the posterior surface is inclined from the lateral surface to the medial surface so that the post 15 comes in contact with the cam 35 in a wide contact area. There is no need to form a predetermined inclination on the cam 35 like the posterior surface of the post 15 and it is sufficient as long as the inclination θ is formed on the posterior surface of the post the same as the inclination θ formed by abduction of the femoral component 30 at the moment when the cam 35 of the femoral component 30 comes in contact with the post 15.

Figure 15:
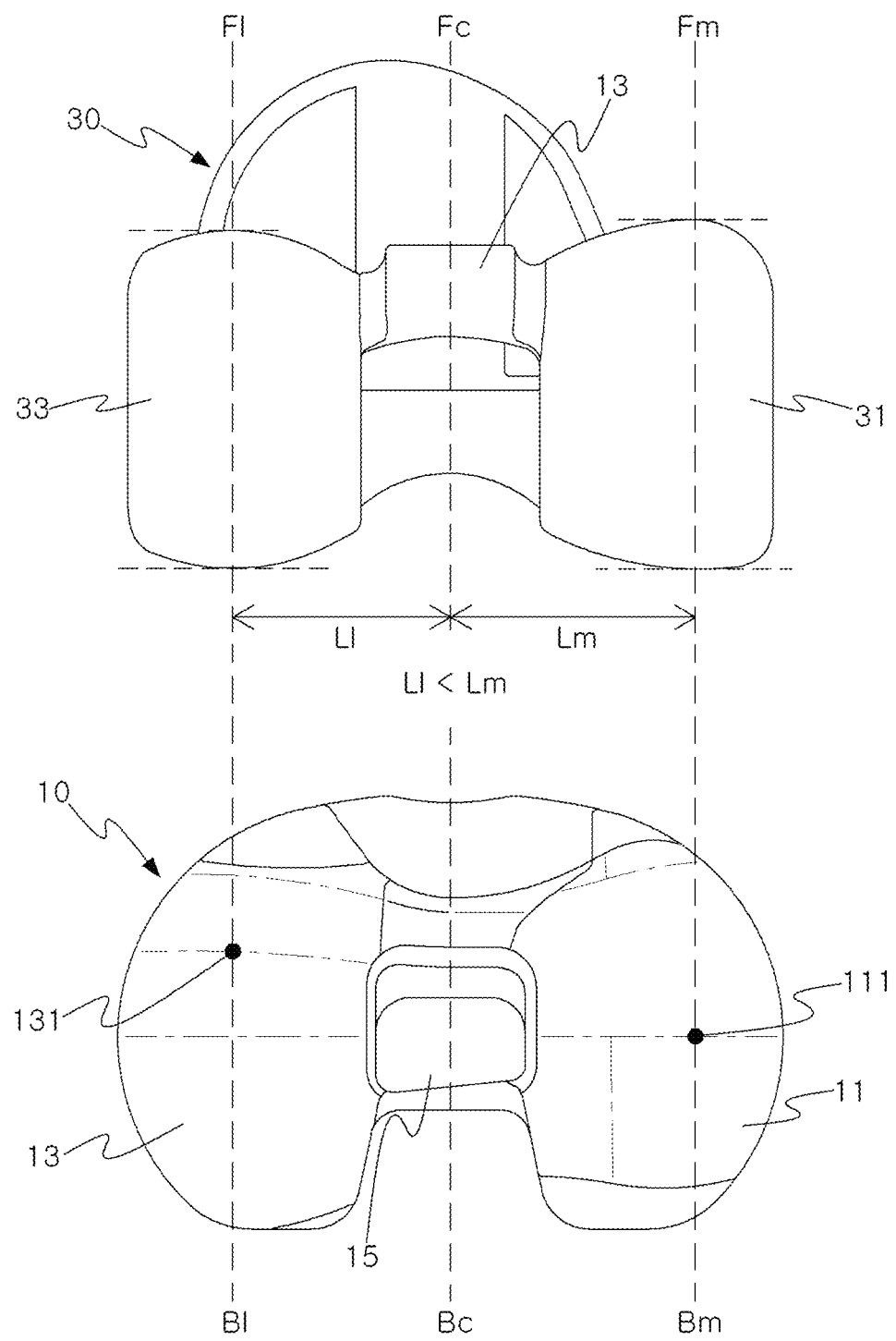
FIG. 15 is a view showing that when the central plane of the bearing member and the central plane of the femoral component are aligned, the distances from the central planes to a medial sulcus-point plane and a medial peak-point plane are the same and the distances from the center to a lateral sulcus-point plane and a lateral peak-point plane are the same.

FIG. 15 is a view showing that when the central plane of the bearing member and the central plane of the femoral component are aligned, the distances from the central planes to a medial sulcus-point plane and a medial peak-point plane are the same and the distances from the center to a lateral sulcus-point plane and a lateral peak-point plane are the same.

The artificial knee joint of the present invention is characterized in that the bearing member 10 and the femoral component 30 are asymmetrically formed respectively in the medial and lateral sides such that the medial sulcus 11 of the bearing member 10 and the medial condyle 31 of the femoral component 30 are the center of motion. In this configuration, in consideration that the femoral component 30 makes motions on the bearing member 10, when the central plane Bc of the bearing member 10 and the central plane Fc of the femoral component 30 are aligned, the distance Lm from the central planes Bc and Fc to the medial sulcus-point plane Bm including the medial sulcus point 111 is made the same as the distance Lm to the medial peak-point plane Fm including the peak points on the medial condyle 31, and the distance L1 from the central planes Bc and Fc to the lateral sulcus-point plane B1 including the lateral sulcus point 131 is made the same as the distance L1 to the lateral peak-point plane F1 including the peak points on the lateral condyle 33. Accordingly, the asymmetric femoral component 30 placed on the bearing 10 can stably make translation, rotation, and roll-back without being dislocated from the bearing member 10.

Figure 16A:
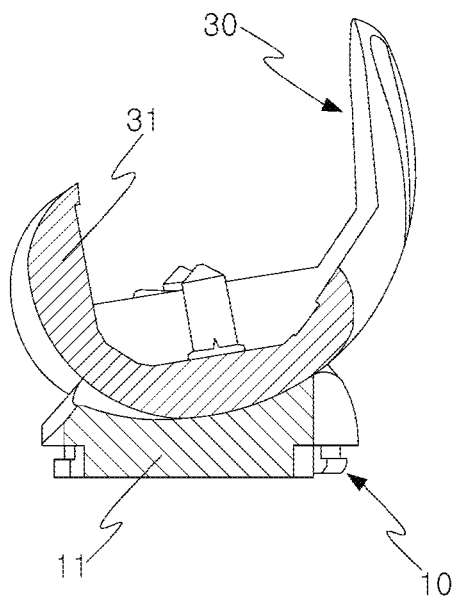
FIG. 16A is a view showing forward movement of the medial condyle in use of the asymmetric artificial knee joint.
Figure 16B:
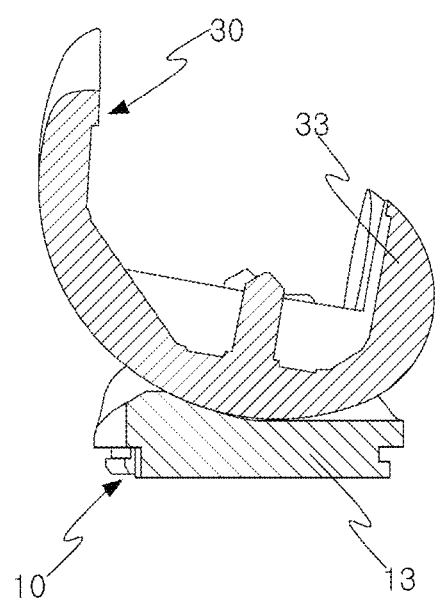
FIG. 16B shows a view showing forward movement of the lateral condyle in use of the asymmetric artificial knee joint.

FIGS. 16A and 16B are a view showing the state in use of the asymmetric artificial knee joint. Referring to FIGS. 16A and 16B to describe the operation of the present invention, the femoral component 30 on the bearing member 10 moves forward on the bearing member 10 in flexion of a knee. FIG. 16A shows forward movement of the medial condyle 31 and FIG. 16B shows forward movement of the lateral condyle 33.

As described above, since the medial sulcus 11 of the bearing member 10 has the medial anterior section 113 and the medial posterior section 115 that each have a predetermined curvature, the distance that the medial condyle 31 can move forward and backward is limited.

In contrast, the lateral condyle 33 is preferably disposed on the lateral sulcus 13 including the lateral anterior section 133 having a curvature smaller than that of the medial anterior section 113, so it can move forward a longer distance than the medial condyle 31. Accordingly, a motion can be made with respect to the medial condyle 31 such that the movement distance of the medial condyle 31 is small and the movement distance of the lateral condyle 33 is large.

In the early stage, the medial condyle 31 and the lateral condyle 33 moved forward together on the bearing member 10, but the medial condyle 31 can move no longer due to the medial anterior section 113 and only the lateral condyle 33 can move further forward. In this process, the surrounding tissues connected to the artificial knee joint are tightened and prevent dislocation of the artificial knee joint, thereby increasing stability. Further, since the lateral condyle 33 is moved with respect to the medial condyle 31, inward biased wear of existing artificial knee joints can be prevented.

The lateral condyle 33 moves forwardly more than the medial condyle 31, thereby generating adduction (internal rotation), but the forward movement is also limited by the tissues around the artificial knee joint. Further, the medial posterior condyle 311 has a uniform curvature, but the lateral posterior condyle 331 increases in curvature toward a posterior direction of the femoral component 30, so it rapidly rotates, whereby the rotation is changed into abduction following the anatomical structure of human body.

Flexion at a large angle of a knee is made after the cam 35 of the femoral component 30 comes in contact with the post 15 of the bearing member 10, but according to the related art, the contact area between the cam 35 and the post 15 is narrow and stress concentration is generated, so the post 15 of the bearing member 10 preferably made of polyethylene is quickly worn.

Accordingly, the post 15 of the bearing 15 is asymmetrically formed such that the posterior surface is inclined from the lateral surface to the medial surface and the abduction angle of the femoral component 30 and the inclination of the posterior surface of the post are made the same at the moment when the cam 35 comes in contact with the post 15 (see FIG. 14), thereby increasing the contact area. Therefore, it is possible to prevent stress concentration and quick wear of the post 15 of the bearing member 10, and to achieve more stable roll-back.

The above description exemplifies the present invention. Further, the description provides an embodiment of the present invention and the present invention may be used in other various combination, changes, and environments. That is, the present invention may be changed or modified within the scope of the present invention described herein, a range equivalent to the description, and/or within the knowledge or technology in the related art. The embodiment shows an optimum state for achieving the spirit of the present invention and may be changed in various ways for the detailed application fields and use of the present invention. Therefore, the detailed description of the present invention is not intended to limit the present invention in the embodiment. Further, the claims should be construed as being including other embodiments.

The invention claimed is:

1. An artificial knee joint comprising:
a bearing member having a top surface that extends between an anterior edge and an opposing posterior edge;
a lateral sulcus recessed into the top surface of the bearing member and having a concave shape, the lateral sulcus having a lateral sulcus point disposed at a maximally recessed location of the lateral sulcus;
a medial sulcus recessed into the top surface of the bearing member and having a concave shape, the medial sulcus having a medial sulcus point disposed at a maximally recessed location of the medial sulcus,
wherein the lateral sulcus point of the lateral sulcus is positioned more forward toward the anterior edge than the medial sulcus point of the medial sulcus such that the medial sulcus is a center of motion and wherein a linear line extends between a point on the anterior edge and a point on the posterior edge and has an anterior-posterior (AP) length, the lateral sulcus point being disposed on the linear line at a distance from the anterior point that is between 10% and 25% of the AP length.

2. The artificial knee joint of claim 1, further comprising:
a central plane centrally extending through the bearing member so as to pass through the anterior edge and the posterior edge, the central plane being vertically extending when the bearing member is horizontally disposed;
a medial sulcus-point plane that is parallel to the central plane and passes through the medial sulcus point;
a lateral sulcus-point plane that is parallel to the central plane and passes through the lateral sulcus point,
wherein the bearing member is formed such that a linear line extending from the central plane to the medial sulcus-point plane at an orientation orthogonal to the central plane is longer than a linear line extending from the central plane to the lateral sulcus point-plane at an orientation orthogonal to the central plane.

3. The artificial knee joint of claim 2, wherein in the bearing member, a lateral posterior section of the lateral sulcus has a curvature smaller than a curvature of a medial posterior section of the medial sulcus.

4. The artificial knee joint of claim 3, wherein the bearing member is asymmetrically formed such that a posterior surface of the bearing member is inclined from a lateral surface to a medial surface.

5. The artificial knee joint of claim 1, further comprising a post protruding between the medial sulcus and the lateral sulcus on the top surface of the bearing member.

6. The artificial knee joint of claim 5, wherein a distance between the lateral sulcus point of the lateral sulcus and the post is smaller than a distance between the medial sulcus point of the medial sulcus and the post.

7. An artificial knee joint comprising:
a bearing member comprising:
a top surface that extends between an anterior edge and an opposing posterior edge;
a lateral sulcus recessed into the top surface of the bearing member and having a concave shape, the lateral sulcus having a lateral sulcus point disposed at a maximally recessed location of the lateral sulcus; and
a medial sulcus recessed into the top surface of the bearing member and having a concave shape, the medial sulcus having a medial sulcus point disposed at a maximally recessed location of the medial sulcus; and
a femoral component having a medial condyle and a lateral condyle disposed on the medial sulcus and the lateral sulcus of the bearing member, respectively,
wherein the lateral sulcus point of the lateral sulcus of the bearing member is positioned more forward toward the anterior edge than the medial sulcus point of the medial sulcus of the bearing member, and wherein when the femoral component is pivoted posterior to anterior on the bearing member, the lateral condyle moves more forward toward the anterior edge than the medial condyle and the medial sulcus of the bearing member and the medial condyle of the femoral component form a center of motion, and
wherein a linear line extends between a point on the anterior edge and a point on the posterior edge and has an anterior-posterior (AP) length, the lateral sulcus point being disposed on the linear line at a distance from the anterior point that is between 10% and 25% of the AP length.

8. The artificial knee joint of claim 7, wherein the bearing member is formed such that a distance from a central plane of the bearing member to a medial sulcus-point plane including the medial sulcus point of the medial sulcus is larger than a distance from the central plane of the bearing member to a lateral sulcus point-plane including the lateral sulcus point of the lateral sulcus, and
the femoral component is formed such that a distance from a central plane of the femoral component to a medial peak-point plane including peak points on the medial condyle is larger than a distance from the central plane of the femoral component to a lateral peak-point plane including peak points on the lateral condyle.

9. The artificial knee joint of claim 8, wherein when the central plane of the bearing member and the central plane of the femoral component are aligned, the distance from the central plane of the bearing member to the medial sulcus-point plane including the medial sulcus point of the medial sulcus is the same as the distance from the central plane of the femoral component to the medial peak-point plane including the peak points on the medial condyle, and
the distance from the central plane of the bearing member to the lateral sulcus point-plane including the lateral sulcus point of the lateral sulcus is the same as the distance from the central plane of the femoral component to the lateral peak-point plane including the peak points on the lateral condyle.

10. The artificial knee joint of claim 9, wherein the femoral component includes a cam connecting the medial condyle and the lateral condyle to each other,
 the bearing member is asymmetrically formed such that a posterior surface of a post upstanding from the top surface of the bearing member is inclined relative to a horizontal plane in which the bearing member is disposed, the posterior surface being inclined from a lateral surface of the post to a medial surface of the post, and
 an inclination of the posterior surface of the post is the same as an angle that is formed by abduction of the femoral component at the moment when the cam of the femoral component comes in contact with the post.

11. The artificial knee joint of claim 10, wherein in the femoral component, a lateral posterior condyle of the lateral condyle has various curvatures in comparison to a medial posterior condyle of the medial condyle.

12. The artificial knee joint of claim 11, wherein in the femoral component, the curvatures of the lateral posterior condyle of the lateral condyle increase toward a posterior direction.

13. An artificial knee joint comprising:
 a bearing member having a top surface that extends between an anterior edge and an opposing posterior edge;
 a lateral sulcus recessed into the top surface of the bearing member and having a concave shape, a maximally recessed area of the lateral sulcus defining a lateral sulcus portion;
 a medial sulcus recessed into the top surface of the bearing member and having a concave shape, a maximally recessed area of the medial sulcus defining a medial sulcus portion;
 wherein the lateral sulcus portion of the lateral sulcus has an anterior side positioned more forward toward the anterior edge than an anterior side of the medial sulcus portion such that the medial sulcus is a center of motion, and wherein a linear line extends between a point on the anterior edge and a point on the posterior edge and has an anterior-posterior (AP) length, the lateral sulcus portion being disposed on the linear line at a distance from the anterior point that is between 10% and 25% of the AP length.

14. The artificial knee joint of claim 13, wherein dimensions of the maximally recessed area of the medial sulcus defining the medial sulcus portion are equal to dimensions of the maximally recessed area of the medial sulcus defining the medial sulcus portion.

* * * * *